United States Patent [19]

Katz

[11] Patent Number: 4,551,456

[45] Date of Patent: Nov. 5, 1985

[54] OPHTHALMIC USE OF NORFLOXACIN AND RELATED ANTIBIOTICS

[75] Inventor: Irving M. Katz, Doylestown, Pa.

[73] Assignee: Merck & Co., Inc., Rahway, N.J.

[21] Appl. No.: 551,775

[22] Filed: Nov. 14, 1983

[51] Int. Cl.$^4$ .................... A61K 31/50; A61K 31/495
[52] U.S. Cl. ...................................... 514/254; 514/912
[58] Field of Search .......................... 424/250; 514/254

[56] References Cited

U.S. PATENT DOCUMENTS

| | | | |
|---|---|---|---|
| 4,146,719 | 3/1979 | Irikura .................................. | 424/250 |
| 4,292,317 | 9/1981 | Pesson .................................. | 424/250 |
| 4,359,578 | 11/1982 | Matsumoto et al. ................ | 424/250 |
| 4,382,892 | 5/1983 | Hayakawa et al. .................. | 544/73 |

FOREIGN PATENT DOCUMENTS 3142854  5/1983  Fed. Rep. of Germany .

OTHER PUBLICATIONS

Chem. Abst. 96: 97219w, (1982)–Sugimoto et al.
Chem. Abst. 96: 97218v, (1982)–Irikura et al.

*Primary Examiner*—Douglas W. Robinson
*Attorney, Agent, or Firm*—William H. Nicholson; Mario A. Monaco

[57] ABSTRACT

Norfloxacin and related antibiotics are useful in the treatment of ocular infections by topical administration.

4 Claims, No Drawings

OPHTHALMIC USE OF NORFLOXACIN AND RELATED ANTIBIOTICS

BACKGROUND OF THE INVENTION

Norfloxacin and structurally related antibiotics are well-known antibacterial agents and are active against a broad spectrum of gram positive and gram negative organisms. Norfloxacin is particularly useful in the treatment of lower urinary tract infections.

SUMMARY OF THE INVENTION

It has now been found that these broad spectrum antibiotics, are compatible with ocular tissue and that therapeutic levels are detected in various ocular tissues and fluids after topical administration and are thus useful for treating a wide variety of bacterial ocular infections by topical administration.

It is therefore an object of this invention to provide topical ophthalmic formulations comprising norfloxacin or a related antibiotic as active ingredient for the treatment of ocular infections.

It is also an object of this invention to provide a method of treating a wide variety of bacterial ocular infections by topical administration of norfloxacin or related antibiotics.

DETAILED DESCRIPTION OF THE INVENTION

The novel compositions of this invention comprise an active ingredient norfloxacin, ofloxacin, pefloxacin, AT-2266 or Bayer 09867, especially norfloxacin, or hydrates or ophthalmologically acceptable salts thereof including acid addition salts such as the hydrochloride, maleate, pamoate or the like and alkali metal salts such as the sodium or potassium salts.

Formulations of these compounds may contain from about 0.03 to 3% and especially 0.15% to 0.6% of medicament although higher or lower dosages can be employed. As a unit dosage from between 0.015 to 1.5 mg, preferably 0.05 to 1.0 mg, and especially 0.1 to 0.3 mg of the compound is generally applied to the human eye, and can be administered as frequently as necessary.

These hereinbefore described dosage values are believed accurate for human patients and are based on the known and presently understood pharmacology of the compounds, and the action of other similar entities in the human eye. They reflect the best mode known. As with all medications, dosage requirements are variable and must be individualized on the basis of the disease and the response of the patient.

In the pharmaceutical preparation the active compound conveniently is admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethyl-cellulose, polyvinylpyrrolidone, isopropyl myristate and other conventionally employed acceptable carriers. The ophthalmological preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, other antibacterial components such as quaternary ammonium compounds, phenylmercuric salts known to have cold sterilizing properties and which are non-injurious in use, thimerosal, methyl and propyl paraben, benzyl alcohol, phenylethanol, buffering ingredients such as sodium chloride, sodium borate, sodium acetate, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium choride vehicles, isotonic sodium borate vehicles and the like. The pharmaceutical preparation may also be in the form of a solid insert.

While many patients find liquid medication to be entirely satisfactory, others may prefer a solid medicament that is topically applied to the eye, for example, a solid dosage form that is suitable for insertion into the cul-de-sac. To this end of the antibiotic can be included with a non-bioerodible insert, i.e. one which after dispensing the drug remains essentially intact, or a bioerodible insert, i.e. one that either is soluble in lacrimal fluids, or otherwise disintegrates. While the insert employed is not critical and those disclosed in U.S. Pat. Nos. 3,630,200 Higuchi; 3,811,444 Heller et al.; 4,177,256 Michaels et al.; 3,868,445 Ryde et al.; 3,845,201 Haddad; 3,981,303 Higuchi; and 3,867,519 Michaels, are satisfactory; in general, however, the inserts described below are found preferable.

For example, one may use a solid water soluble polymer as the carrier for the medicament. The polymer used to form the insert may be any water soluble non-toxic polymer, for example, cellulose derivatives such as methylcellulose, sodium carboxymethyl cellulose, or a hydroxy lower alkyl cellulose such as hydroxyethyl cellulose, hydroxypropyl cellulose, hydroxypropylmethyl cellulose and the like; acrylates such as polyacrylic acid salts, ethyl acrylates, polyacrylamides; natural products such as gelatin, alginates, pectins, tragacanth, karaya, chondrus, agar, acacia; the starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, and mixtures of said polymer.

The ophthalmic formulation may also be in the form of a clear physiologically-acceptable liquid which forms a semi-solid "gel" at human body temperatures. Polymers having these properties are tetra substituted derivatives of ethylene diamine (poloxamine, $w=2$ in Formula I), propylene diamine ($w=3$), butylene diamine ($w=4$), pentylene diamine ($w=5$) or hexylene diamine ($w=6$). The substitutents are block copolymers of poly(oxypropylene) and poly(oxyethylene) of various chain lengths and ratios x to y in the general formula of the polymer shown below.

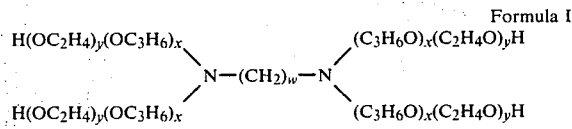

Formula I wherein w is an integer from 2 through 6.

A typical polymer system would contain a polymer containing approximately 40 to 80% poly(oxyethylene) and approximately 20 to 60% poly(oxypropylene). The total molecular weight of the polymer used is at a minimum about 7,000 and can go as high as 50,000 but preferably is in the range of 7,000 to 30,000; and x and y are any integers within the above constraints. Preferred polymers are those of the formula above where w=2, namely the poloxamine polymer.

The aqueous drug delivery vehicle would contain from 10% to 50% by weight of the entire vehicle as polymer described above. The aqueous drug delivery vehicle would also contain the drug or therapeutic agent in addition to various additives such as acids or bases to adjust the pH of the composition, buffers to maintain the pH, preservatives to control bacterial contamination, other additives to provide for drug solubility and stability and formulation performance with purified water making up the remainder of the drug delivery vehicle.

| Formulation of 0.3% Solution | |
|---|---|
| Ingredient | mg/ml |
| EXAMPLE 1 | |
| Norfloxacin | 3 |
| sodium acetate 3H$_2$O | 2.72 |
| benzalkonium Chloride | 0.11 |
| ethylenediamine tetra-acetic acid, disodium salt | 0.10 |
| sodium Chloride | 7.42 |
| hydrochloric acid to pH | 5.2 |
| water | q.s. |
| EXAMPLE 2 | |
| Norfloxacin hydrochloride | 3 mg. |
| petrolatum q.s. ad. | 1 gram |
| EXAMPLE 3 | |
| Norfloxacin hydrochloride | 1 mg. |
| Hydroxypropylcellulose q.s. | 12 mg. |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circuits in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

What is claimed is:

1. A method of treating ocular bacterial infections which comprises topical ocular administration to an infected eye, of 0.015–1.5 mg of an antibiotic selected from norfloxacin, ofloxacin, pefloxacin, AT-2266 and Bayer 09867, hydrates or ophthalmologically acceptable salts thereof.

2. The method of claim 1 wherein the antibiotic is norfloxacin, a hydrate or ophthalmologically acceptable salt thereof.

3. The method of claim 2 wherein the norfloxacin is administered as an aqueous solution.

4. The method of claim 1 wherein the carrier is a clear physiologically-acceptable liquid which forms a semi-solid gel at human body temperatures.

* * * * *